US005569922A

United States Patent [19]
Clarke

[11] Patent Number: 5,569,922
[45] Date of Patent: Oct. 29, 1996

[54] PORTABLE FUEL ANALYZER FOR THE DIAGNOSIS OF FUEL-RELATED PROBLEMS ON-SITE AT THE VEHICLE SERVICE BAY

[75] Inventor: Richard H. Clarke, Big Sky, Mont.

[73] Assignee: Boston Advanced Technologies, Inc., Newton, Mass.

[21] Appl. No.: 507,724

[22] Filed: Jul. 26, 1995

[51] Int. Cl.$^6$ ............................ G01N 21/35; G01N 33/22
[52] U.S. Cl. .................................... 250/339.12; 250/341.5
[58] Field of Search ........................ 290/339.12, 339.13, 290/341.5, 343; 123/1 A; 73/116, 117.2

[56] References Cited

U.S. PATENT DOCUMENTS

| | | | |
|---|---|---|---|
| 3,973,848 | 8/1976 | Jowett et al. | 250/345 |
| 4,323,777 | 4/1982 | Baskins et al. | 250/339 |
| 4,620,284 | 10/1986 | Schnell et al. | 364/498 |
| 4,963,745 | 10/1990 | Maggard | 250/343 |
| 5,046,355 | 9/1991 | Tack et al. | 73/61.4 |
| 5,126,570 | 6/1992 | Boos | 250/343 |
| 5,139,334 | 8/1992 | Clarke | 356/301 |
| 5,205,151 | 4/1993 | Shimamura et al. | 73/1 |
| 5,225,679 | 7/1993 | Clarke et al. | 250/343 |
| 5,412,581 | 5/1995 | Tackett | 250/339.12 |

FOREIGN PATENT DOCUMENTS

| | | |
|---|---|---|
| 0285251 | 10/1988 | European Pat. Off. . |
| 197810 | 10/1978 | United Kingdom . |

OTHER PUBLICATIONS

*Changes in Gasoline II*, Downstream Alternatives, Inc. Bremen, IN, Jul. 1992.

Kelly et al., "Prediction of Gasoline Octane Numbers from Near-Infrared Spectral Features in the Range of 660-1215 nm," *Analytical Chemistry*, 61:4, 313 (Feb., 1989).

Louw and Richards, "A Simple Directly Combined Gas Chromatographic-Infrared Spectrometric System for Identification of Low Molecular Weight Hydrocarbons," *Applied Spectroscopy*, 29:1, 15-24 (1975).

Telfair et al., "A microcomputer-controlled infrared analyzer for multi-component analysis," *American Laboratory*, 8:11, 91-100 (Nov., 1976).

Primary Examiner—Davis L. Willis
Assistant Examiner—Richard Hanig
Attorney, Agent, or Firm—Thomas J. Engellenner

[57] ABSTRACT

Method and apparatus for diagnosing fuel-related problems at the site of vehicle servicing and matching fuels to new engine designs. Fuel properties associated with a fuel sample can be measured with mid-infrared analysis. The measured fuel property values can be compared with predetermined preferred values for the fuel properties for the particular type of vehicle. Fuel-related problems can then be identified and diagnosed based upon this comparison, and the diagnosis can be immediately displayed for the operator. In one embodiment, driveability index can be determined in situ and in real time. In other embodiments, octane number, and Reid vapor pressure can be similarly determined.

16 Claims, 2 Drawing Sheets

PORTABLE FUEL ANALYZER FOR THE DIAGNOSIS OF FUEL-RELATED PROBLEMS ON-SITE AT THE VEHICLE SERVICE BAY

BACKGROUND OF THE INVENTION

The field of the present invention is the diagnosis of engine problems and, in particular, methods and devices for the diagnosis of fuel-related problems.

In many cases, an automobile brought in for servicing because of poor performance is not experiencing a mechanical problem, but rather a fuel problem. However, the diagnosis of fuel-related problems is often hampered by the lack of fuel analyzing equipment at the site of vehicle service. In addition, fuel-related problems can have diverse manifestations, including engine starting failures; engine performance difficulties such as engine hesitation, roughness and stalling after starting or upon de-acceleration around a curve; engine detonation difficulties; engine loss of power; poor engine fuel economy; engine missing and surging; noxious engine fumes; and smoky engine exhaust.

Determination of octane number and Reid vapor pressure are some of the most well known ways of characterizing a fuel. The octane number is a measure of a fuel's ability to resist engine knocking. Engine knocking results when a fuel fails to burn smoothly and evenly, and the resulting unburned portion of the air/fuel mixture explodes violently from spontaneous combustion. Octane number is conventionally determined and stated according to ASTM methods. For example, a research octane number (RON) can be determined according to ASTM Method 2699-84, and a motor octane number (MON) can be determined according to ASTM Method 2700-84. The conventional pump octane rating is determined as one-half the sum of RON plus MON.

Reid vapor pressure is a measure of a fuel's "front end volatility" or more volatile components. It can be measured by performing a "Reid Method" test procedure whereby a gasoline sample, which is sealed in a metal chamber, is submerged in a 100° F. water bath. Higher readings are determined for the more volatile fuels because such components vaporize more readily, thus creating more pressure on the measurement device. Lower readings are determined for the less volatile fuels because such components create less vapor.

Various methods are known for the evaluation of octane number, Reid vapor pressure and other fuel properties. However, because these analytical tools are typically not available to automobile mechanics, there exists a need to provide a simple and relatively inexpensive method and device for quickly and reliably diagnosing fuel-related problems at the site of vehicle service.

SUMMARY OF THE INVENTION

The present invention is based on the recognition that fuel-related problems can be simply and relatively inexpensively diagnosed by using mid-infrared analysis to measure the fuel properties related to such problems, such as driveability index, and comparing these measured values with the preferred values for a particular model and type of vehicle. The diagnosis of fuel-related problems can be performed at the site of vehicle servicing to provide a quick and reliable evaluation of a potentially fuel-related problem. Further, such a diagnosis can be used for matching an optimal fuel to a new engine design.

Accordingly, in one aspect of the invention, fuel properties associated with a fuel sample can be measured with mid-infrared analysis. The measured fuel property values can be compared with pre-determined preferred values for the fuel properties for the particular type of vehicle. Fuel-related problems can then be identified and diagnosed based upon this comparison, and the diagnosis can be immediately displayed for the operator. The term "display", as used herein, describes a transient visual display as well as other more permanent records, such as hard copy print outs.

In an embodiment of the invention, driveability index can be one of the fuel properties which is measured and used to diagnose fuel-related problems. Driveability index is conventionally determined and stated according to the known ASTM D-86 method. According to this method, three distillation temperatures, T10, T50, and T90 are determined for a sample. T10, T50, and T90 correspond to the temperatures at which 10 percent, 50 percent, and 90 percent, respectively, of the sample are distilled off. The driveability index for the sample is then determined according to the following equation:

$$\text{Driveability index} = 1.5\ (T10) + 3.0\ (T50) + 1\ (T90)$$

In contrast to the conventional methods for measuring driveability index, an embodiment of the invention involves measuring fuel properties, such as driveability index, by illuminating a fuel sample with mid-infrared light and detecting absorbance values associated with the components of the fuel. The detected absorbance values can be correlated with a matrix of pre-determined coefficients associated with the fuel components and pre-determined values of the fuel property. The detected absorbance values can be multiplied by their corresponding pre-determined coefficients and the resulting absorbance-coefficient products can be summed to determine the value of the fuel property, such as driveability index, associated with the sample.

Alternatively, in another embodiment of the invention, detected absorbance values for a fuel sample can be correlated with a matrix of pre-determined coefficients associated with the fuel components of the sample and pre-determined T10 values. The detected absorbance values can be multiplied by their correlated pre-determined coefficients and the resulting absorbance-coefficient products can be summed to determine a T10 value associated with the sample. Similarly, detected absorbance values can be correlated with matrices of pre-determined coefficients associated with the fuel components of the sample and pre-determined T50 and T90 values. The detected absorbance values can be multiplied by their correlated pre-determined coefficients and the resulting absorbance-coefficient products can be summed to determine T50 and T90 values for the sample. The determined T10, T50 and T90 values can then be inserted into the standard driveability index equation to obtain a driveability index associated with the sample.

In further embodiments of the invention, fuel properties such as octane number and Reid vapor pressure can be measured and used to diagnose fuel-related problems.

The invention further encompasses analytical devices for diagnosis of fuel-related problems. The devices can include a measurement means for measuring fuel property values through mid-infrared analysis; a comparison means for comparing measured fuel property values with pre-determined preferred value ranges for the fuel properties for a particular vehicle; a diagnosis means for diagnosing fuel-related problems based upon the results of the comparison; and a display means for displaying a result of the diagnosis.

In an embodiment of the invention, the device can be used to measure the driveability index associated with a sample to diagnose fuel-related problems. In another embodiment of the invention, the measurement means for measuring fuel property values, such as driveability index, can include a mid-infrared light source for illuminating the sample; a detector for detecting absorbance values associated with fuel components; and a correlating means for correlating the detected absorbance values with a matrix of pre-determined coefficients associated with the fuel components and pre-determined values of the fuel property; a multiplying means for multiplying the detected absorbance values by their correlated pre-determined coefficients; and a summing means for summing the resulting absorbance-coefficient products to determine value of the fuel property, such as driveability index, associated with the sample.

In still another embodiment of the invention, the measurement means can include a mid-infrared light source for illuminating the sample; a detector for detecting absorbance values associated with fuel components; a correlating means for correlating the detected absorbance values with a matrices of pre-determined coefficients associated with the fuel components and pre-determined T10 values, T50 values, and T90 values; a multiplying means for multiplying the detected absorbance values by their correlated pre-determined coefficients; a summing means for summing the resulting absorbance-coefficient products to determine values of T10, T50 and T90 associated with the sample, and a determination means for determining the driveability index of the sample based upon the determined T10, T50 and T90 values.

In further embodiments of the invention, the devices can measure the octane number and/or the Reid vapor pressure of a fuel sample to diagnose fuel-related problems. The devices can be portable and can include an on-site fuel diagnosis capability for use in a service bay. The devices can further include a data communication means for communicating with a remote computer. Moreover, the devices can be used to diagnose diverse fuel-related problems, such as engine starting failures; engine performance difficulties such as engine hesitation, roughness and stalling after starting or upon de-acceleration around a curve; engine detonation difficulties; engine loss of power; poor engine fuel economy; engine missing and surging; noxious engine fumes; and smoky engine exhaust.

In still another aspect of the invention, the devices of the present invention can be used to match a new engine design with its optimal fuel. New engines can be tested under a variety of conditions, and the present invention's devices can be used to identify the recommended fuel properties for a new engine design. The devices can include a mid-infrared analysis means for measuring fuel property values; a comparison means for comparing measured fuel property values with pre-estimated preferred value ranges for the fuel properties for a new engine design; a diagnosis means for diagnosing fuel-related problems based upon the results of the comparison; and a display means for displaying a result of the diagnosis.

BRIEF DESCRIPTION OF THE DRAWINGS

These and other features and advantages of the present invention will be more fully understood by reference to the following detailed description in conjunction with the attached drawings in which like reference numerals refer to like elements and in which.

DETAILED DESCRIPTION OF THE INVENTION

Figure 1:
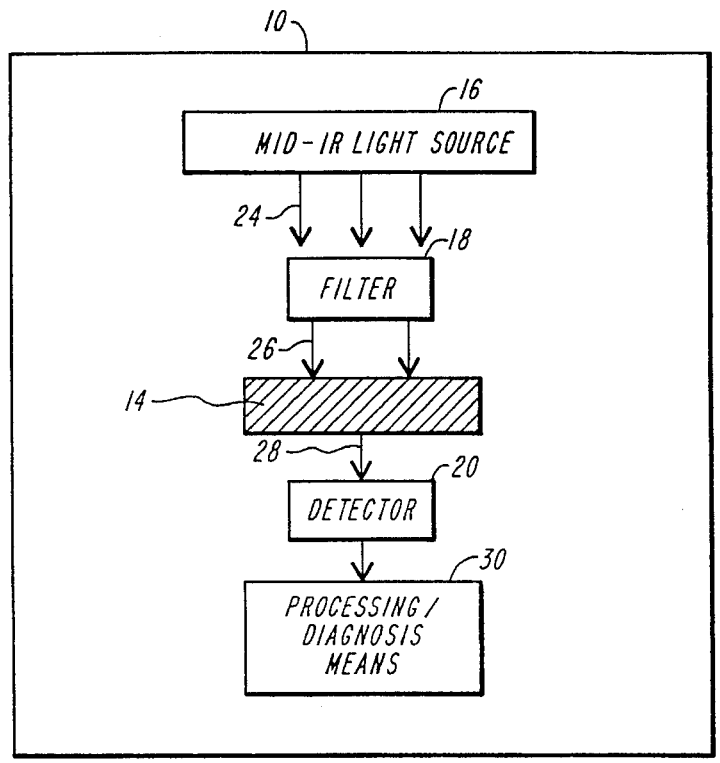
FIG. 1 is a schematic representation of a mid-infrared fuel properties monitor according to an embodiment of the invention to detect and to evaluate fuel properties for the diagnosis of fuel-related problems.

FIG. 1 is a schematic representation of a mid-infrared fuel properties monitor 10 for detection and evaluation of components and properties of a fuel sample 14 contained in an examination vessel 12 according to an embodiment of the invention. The monitor 10 illustrated in FIG. 1 is equipped with a mid-infrared light source 16, a filter 18, a detector 12, and a processing diagnosis means 30.

Mid-infrared analysis in the practice of the present invention can involve illuminating a fuel sample with mid-infrared light in a range of about 2.5 µm to about 20 µm. The molecules of the fuel components of the sample can each exhibit characteristic primary, overtone and/or combination vibrational modes (also referred to herein as "signature" or "signature modes") when excited in narrow wavelength bandwidths associated with particular fuel components. These signatures can be exhibited in terms of absorbances of the mid-infrared light. Such absorbances can be detected and correlated with matrices of pre-determined coefficients associated with the fuel components and pre-determined fuel property values. The detected absorbance values can be multiplied by their correlated coefficients, and the resulting absorbance-coefficient products can be summed to determine property values associated with the sample.

For exemplary purposes, FIG. 1 illustrates a detector assigned to methanol (MEOH) detection. Notwithstanding, in the practice of the invention, other detectors can be included and assigned specifically to the detection of ethanol (ETOH), tertiary butyl alcohol (TBA), Methyl tertiary butyl ether (MTBE), di-isopropyl ether (DIPE), ethyl tertiary butyl ether (ETBE), tertiary amyl methyl ether (TAME), metaxylene, toluene, and benzene. Further, two detectors can be assigned to the detection of aromatics since aromatic molecular structures can be detected at both shorter and longer wavelengths. Similarly, two detectors can be assigned to the detection of olefins which also can be detected at two different wave lengths. A separate detector can be assigned to the detection of straight chain hydrocarbons.

A separate detector can also be assigned to the detection of alkylates for use as a correction factor. A high percentage of alkylates in the fuel sample can raise the total absorbance spectrum and can lead to false readings for other fuel components (e.g., MBTE). Accordingly, the absorbance values for other fuel components can be adjusted to take into account the alkylates' effect once the alkylates' concentration is known.

Still another detector can be assigned as a reference detector for use as a correction factor. The reference detector can operate in that part of the absorbance spectrum where there is very little absorbance. Stated a little differently, the reference detector can operate in an "absorbance window". Some fuels can show absorbance in such an absorbance window, however. Thus, to normalize absorbance detection among various fuels, the absorbance values for the other fuel components can be adjusted to take into account absorbance detected in the absorbance window.

Alternatively, a single broad band detector 12 can be used for the detection of multiple fuel components in the fuel sample.

In the embodiment of FIG. 1, the mid-infrared light source 16 can be provided on one side of the fuel-containing examination vessel 12 for illuminating the fuel 14 contained within the vessel. The detector 20 can be provided on the other side of the vessel 12 for the detection of absorption associated with the presence of the assigned fuel component. Because each detector of the invention can be assigned to a specific fuel component of interest, each detector's input can be limited to that narrow portion of the mid-infrared spectrum which is associated with a selected vibrational mode signature and which has been determined to be characteristic of the assigned fuel component.

Isolation of each detector to an assigned fuel component can be achieved in this embodiment by interposing the filter 18 between the light source 16 and the detector 20. Light 24 from the mid-infrared light source 16 can enter the filter 18 and a narrow vibrational mode or wavelength 28 appropriate for the assigned fuel component being measured can exit the filter to enter the detector 20. Table 1 shows an exemplary array of such filters.

TABLE 1

FUEL COMPONENT FILTER ARRAY

| Fuel Component | Filter No. | Center Wavelength, $\lambda_c$ μm | Bandwidth 1% of $\lambda_c$ μm | Center Frequency $cm^{-1}$ |
|---|---|---|---|---|
| Reference | 17 | 4.80 | .0480 | 2083 |
| MEOH | 1 | 9.70 | .0970 | 1031 |
| ETOH | 2 | 9.52 | .0952 | 1054 |
| TBA | 3 | 10.93 | .1093 | 915 |
| MTBE | 4 | 8.30 | .0830 | 1205 |
| DIPE | 5 | 8.63 | .0863 | 1159 |
| ETBE | 6 | 8.95 | .0895 | 1117 |
| TAME | 7 | 8.42 | .0842 | 1188 |
| Gen. Arom. 1 | 8 | 6.23 | .0623 | 1605 |
| Metaxylene | 9 | 13.53 | .1353 | 739 |
| Toluene | 10 | 13.72 | .1372 | 729 |
| Benzene | 11 | 14.79 | .1479 | 676 |
| Gen. Arom. 2 | 12 | 13.00 | .1300 | 769 |
| Alkylate Corr | 13 | 7.32 | .0732 | 1366 |
| Olefins | 14 | 10.35 | .1035 | 966 |
| Straight Chain HCs | 15 | 3.51 | .0351 | 2852 |
| Olefins | 16 | 6.06 | .0606 | 1650 |

Additional filters and detectors can be employed for the detection of the other above-identified fuel components of interest. In addition, each filter can take the form of a window on a detector device itself, rather than as a separate discrete component. Further, the filter can even be eliminated where the detection is otherwise limited to a narrow band of interest.

Figure 2:
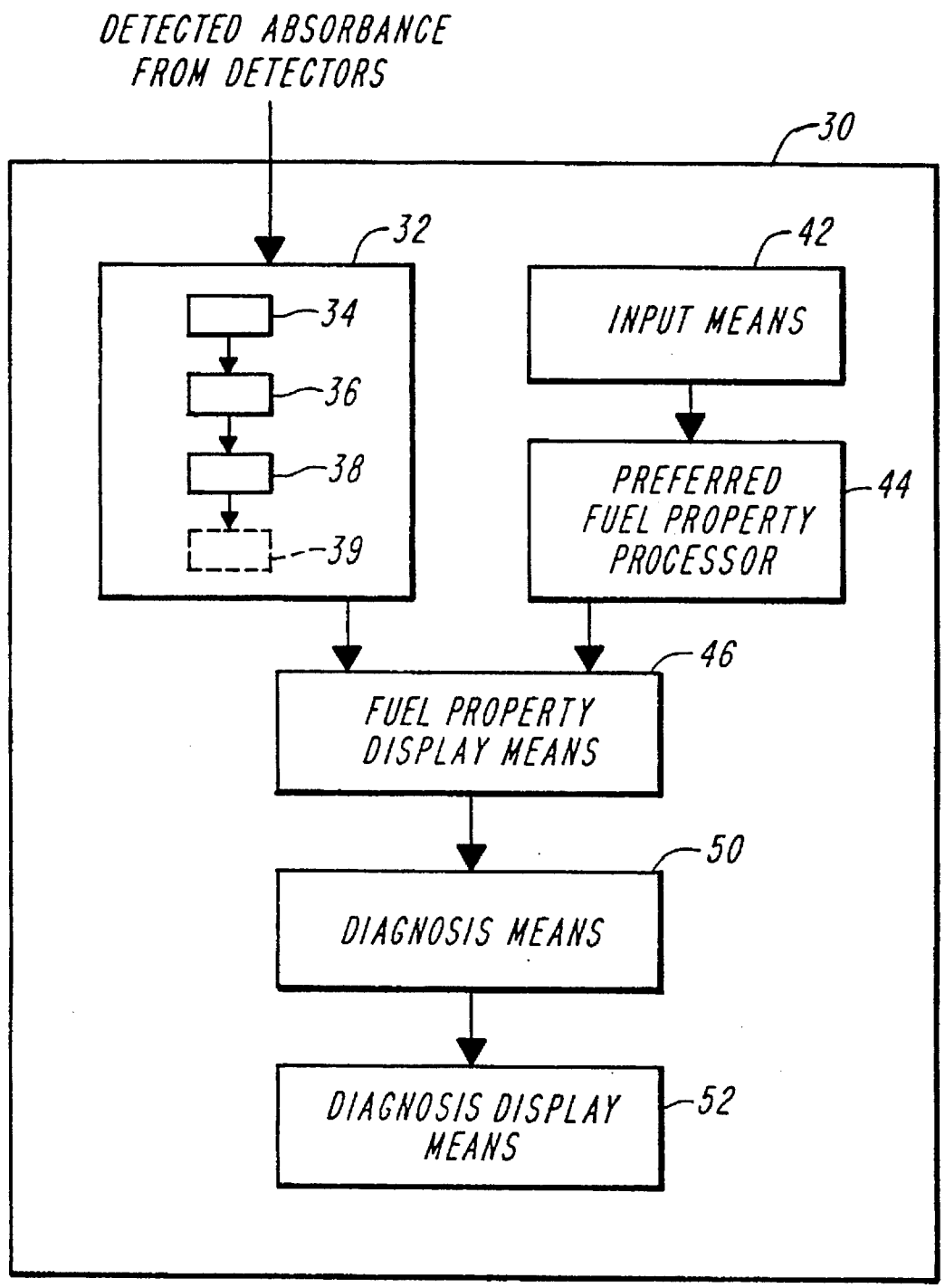
FIG. 2 illustrates the processing of absorption detection signals according to an embodiment of the invention to determine and to compare actual and preferred values for fuel properties associated with a fuel sample to diagnose a fuel-related problem for a particular vehicle.

FIG. 2 is a schematic representation of a processing/diagnosis means 30 having a sample fuel property processor 32 containing a correlating means 34, a multiplying means 36, a summing means 38 and an optional determination means 39; an input means 42; a preferred fuel property processor 44; a fuel property display means 46; a diagnosis means 50; and a diagnosis display means 52, according to an embodiment of the invention.

In the practice of the invention, detected absorbance signal outputs from the detectors can be fed into the sample fuel property processor 32 of the processing/diagnosis means 30 for processing and displaying the results of the diagnosis of the fuel-related problem. Inside the processor 32, the correlating means 34 can correlate the detected absorbance values (e.g., $A_1+A_2+\ldots A_{17}$) associated with the particular fuel components with a matrix of pre-determined coefficients (e.g., $C_1+C_2+\ldots C_{17}$) associated with the fuel components and pre-determined values of the fuel property being measured. For example, an absorbance value (e.g., $A_1$) associated with MEOH can be correlated with a pre-determined coefficient (e.g., $C_{1di}$) associated with methanol and driveability index. The multiplying means 36 can multiply the detected absorbance values by the correlated pre-determined coefficients to obtain a plurality of absorbance-coefficient products. The summing means 38 can then determine the fuel property associated with the sample by summing the resulting absorbance-coefficient products. For example, the driveability index of a sample can be determined according to the following equation:

Sample Driveability Index=$C_{di1}A_1+C_{di2}A_2+\ldots C_{di17}A_{17}$

In an alternative embodiment of the invention, the correlating means 34 can correlate the detected absorbance values (e.g., $A_1+A_2+\ldots A_{17}$) associated with the fuel components with a matrix of pre-determined coefficients (e.g., $C_{1T10}+C_{2T10}+\ldots C_{17T10}$) associated with the fuel components and pre-determined values of T10. Similarly, the correlating means 34 can correlate the detected absorbance values (e.g., $A_1+A_2+\ldots A_{17}$) associated with the fuel components with matrices of pre-determined coefficients associated with the fuel components and pre-determined values of T50 and T90. The multiplying means 36 can multiply the detected absorbance values by the correlated pre-determined coefficients to obtain a plurality of absorbance-coefficient products. The summing means 38 can then sum the resulting absorbance-coefficient products to determine the T10, T50 and T90 values associated with the sample according to the following equations:

Sample T10=$C_{1T10}A_1+C_{2T10}A_2+\ldots C_{17T10}A_{17}$

Sample T50=$C_{1T50}A_1+C_{2T50}A_2+\ldots C_{17T50}A_{17}$

Sample T90=$C_{1T90}A_1+C_{2T90}A_2+\ldots C_{17T90}A_{17}$

The determination means 39 can determine the driveability index for the sample by inserting the T10, T50 and T90 values determined for the sample into the standard driveability index equation.

Notwithstanding the foregoing, the content of some fuel components is specified at the pump (e.g., alcohol). Therefore, a simplified embodiment of the invention is programmed with the known alcohol content of the fuel supply under testing, and the present detection function is then limited to other fuel components. Thereafter, total fuel properties are computed as otherwise set forth herein.

The value for the fuel property associated with the sample determined by processor 32 can be compared with the preferred value for the fuel property for a particular vehicle. The preferred fuel property processor 44 can correlate vehicle identification information entered by an operator via the input means 42 with the preferred value for the fuel property in a look-up table. The sample and preferred fuel property values can then be fed into, compared and displayed with the fuel property display means 46.

The actual and preferred values of the fuel property can then be fed into the diagnosis means 50. The diagnosis means 50 can correlate the comparison between the actual and preferred fuel property values with a fuel-related problem in a look-up table. For example, if the actual driveability index is 1350 and the preferred driveability index is 1100, the diagnosis means 50 can determine that the comparison between actual and preferred driveability index values indicates a potential problem for starting in cold weather and can display the result of this diagnosis. Table 2 provides a non-inclusive list of fuel properties, such as driveability index, which are relevant to particular fuel-related problems.

TABLE 2

FUEL PROPERTIES RELEVANT TO PARTICULAR FUEL-RELATED PROBLEMS

| Fuel Property | Fuel-Related Problem |
| --- | --- |
| Fuel Volatility | |
| Driveability Index | Cool weather driveability problems, hot start and hot driveability problems, vapor lock, evaporative losses, crankcase deposits, combustion chamber and spark plug deposits |
| Reid Vapor Pressure | Low temperature starting problems, evaporative losses, vapor lock |
| Vapor Liquid (V/L) Ratio | Vapor lock |
| Octane Number | |
| Research Octane Number (RON) | Low to medium speed knock and run-on |
| Motor Octane Number (MON) | High speed knock/Part-throttle knock |
| Copper Corrosivity | Fuel system corrosion |
| Stability | |
| Existent Gum | Induction system deposits, filter clogging |
| Oxidation Stability | Storage life limitations |
| Sulfur Content | Exhaust emissions, engine deposits and engine wear |
| Metallic additives (lead and others) | Catalyst deterioration (unleaded vehicles) |
| Temperature for Phase Separation | Water intolerance of blended fuels |

The diagnosis means 50 can also determine an overall rating for fuel quality. For example, an actual driveability index of 1350 in comparison with a preferred driveability index of 1100 can indicate an unacceptable fuel quality for the particular vehicle.

The diagnosis means 50 can then feed the results of the diagnosis into the diagnosis display means 52 which can display the results of the diagnosis.

Figure 3:
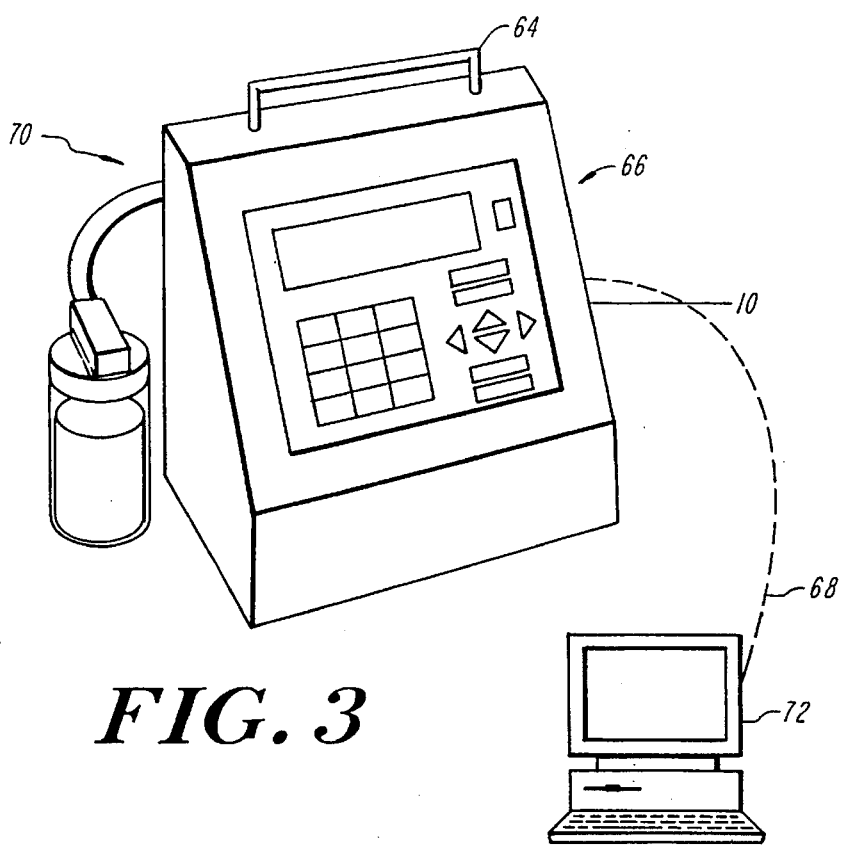
FIG. 3 illustrates an exterior view of a device, according to an embodiment of the invention.

FIG. 3 illustrates an exterior view of the device 70 of the present invention. The device 70 can be portable and can be carried by handle 64. The monitor 10 can be encased in a material 66 that can have the resilience and durability for use in a service bay. The monitor 10 can also be equipped with the means 68 for communicating with a remote computer 72.

In still another aspect, the devices of the present invention can be used to match a new engine design with its optimal fuel. New engines can be tested under a variety of conditions both in the laboratory and in real-world road situations. When the new engine performance is less than expected, the devices of the present invention can be used to characterize the components of the fuel. When the new engine performance is as expected or desired, the present invention's devices can be used to identify the ranges of the fuel properties to be recommended for the new engine. In the practice of this aspect of the invention, pre-estimated preferred fuel property values in lieu of vehicle identification information can be entered into input means 44.

In sum, the present invention benefits from the recognition that fuel-related problems can be simply and relatively inexpensively diagnosed by using mid-infrared analysis to measure the fuel properties, such as driveability index, related to such problems. It will be understood that the above description pertains to only several embodiments of the present invention. That is, the description is provided by way of illustration and not by way of limitation. For example, other fuel properties not specifically discussed herein can be relevant to fuel-related problems and accordingly, can be evaluated by still other embodiments of the present invention. The invention is further characterized according to the following claims:

What is claimed is:

1. A method for diagnosing potential fuel-related problems associated with a hydrocarbon fuel sample comprising the steps of:

measuring a value for at least one fuel property associated with the sample through a mid-infrared analysis;

comparing the value measured for the fuel property with a pre-determined preferred value range for the fuel property for a particular vehicle;

diagnosing the fuel-related problem based upon the result of the comparison step; and displaying a result of the diagnosis step.

2. The method of claim 1 wherein the step of wherein the step of measuring the value for the fuel property associated with the sample through mid-infrared analysis further comprises measuring the value for a driveability index associated with the sample.

3. The method of claim 1 wherein the step of measuring the value for the fuel property associated with the sample through mid-infrared analysis further comprises the steps of:

illuminating the sample with mid-infrared light;

detecting a plurality of absorbance values associated with a plurality of fuel components in the sample;

correlating the detected absorbance values with a matrix of a plurality of pre-determined coefficients associated with the fuel components and a plurality of pre-determined values of the fuel property;

multiplying the detected absorbance values by the correlated pre-determined coefficients to obtain a plurality of absorbance-coefficient products; and summing the absorbance-coefficient products to determine the value of the fuel property associated with the sample.

4. The method of claim 2 wherein the step of measuring the value for the fuel property associated with the sample through mid-infrared analysis further comprises the steps of:

illuminating the sample with mid-infrared light;

detecting a plurality of absorbance values associated with a plurality of fuel components in the sample;

correlating the detected absorbance values with a matrix of a plurality of pre-determined coefficients associated with the fuel components and a plurality of pre-determined T10 values, a matrix of a plurality of pre-determined coefficients associated with the fuel components and a plurality of pre-determined T50 values, and a matrix of a plurality of pre-determined coefficients associated with the fuel components and a plurality of pre-determined T90 values;

multiplying the detected absorbance values by the correlated pre-determined coefficients to obtain a plurality of absorbance-coefficient products; and summing the absorbance-coefficient products to determine a T10 value, a T50 value and a T90 value associated with the sample; and determining the driveability index associated with the sample based upon the determined T10, the T50 and the T90 values.

5. The method of claim 1 wherein the step of measuring the value for the fuel property associated with the sample through mid-infrared analysis further comprises measuring the value for an octane number associated with the sample.

6. The method of claim 1 wherein the step of wherein the step of measuring the value for the fuel property associated with the sample through mid-infrared analysis further comprises measuring the value for a Reid vapor pressure associated with the sample.

7. An apparatus for diagnosing potential fuel-related problems associated with a hydrocarbon fuel sample comprising:

a measurement means for measuring a value for at least one fuel property associated with the sample through a mid-infrared analysis;

a comparison means for comparing the value measured for the fuel property with a pre-determined preferred value range for the fuel property for a particular vehicle;

a diagnosis means for diagnosing the fuel-related problem based upon a result of the comparison; and a display means for displaying a result of the diagnosis.

8. The apparatus of claim 7 wherein the measurement means further comprises means for determining driveability index.

9. The apparatus of claim 7 wherein the measurement means further comprises:

a mid-infrared light source for illuminating the sample;

a detector for detecting a plurality of absorbance values associated with a plurality of fuel components in the sample;

a correlating means for correlating the detected absorbance values with a matrix of a plurality of pre-determined coefficients associated with the fuel components and a plurality of pre-determined values of the fuel property;

a multiplying means for multiplying the detected absorbance values by the correlated pre-determined coefficients to obtain a plurality of absorbance-coefficient products; and a summing means for summing the absorbance-coefficient products to determine the value of the fuel property associated with the sample.

10. The apparatus of claim 8 wherein the measurement means further comprises:

a mid-infrared light source for illuminating the sample;

a detector for detecting a plurality of absorbance values associated with a plurality of fuel components in the sample;

a correlating means for correlating the detected absorbance values with a matrix of a plurality of pre-determined coefficients associated with the fuel components and a plurality of pre-determined T10 values, a matrix of a plurality of pre-determined coefficients associated with the fuel components and a plurality of pre-determined T50 values, and a matrix of a plurality of pre-determined coefficients associated with the fuel components and a plurality of pre-determined T90 values;

a multiplying means for multiplying the detected absorbance values by the correlated pre-determined coefficients to obtain a plurality of absorbance-coefficient products;

a summing means for summing the absorbance-coefficient products to determine a T10 value, a T50 value and a T90 value associated with the sample; and a determination means for determining the driveability index associated with the sample based upon the determined T10, the T50 and the T90 values.

11. The apparatus of claim 7 wherein measurement means further comprises a means for determining octane number.

12. The apparatus of claim 7 wherein measurement means further comprises a means for determining Reid vapor pressure.

13. The apparatus of claim 7, wherein the apparatus is a portable apparatus.

14. The apparatus of claim 7, wherein the apparatus further comprises a casing for use in a service bay.

15. The apparatus of claim 7, wherein the apparatus further comprises a data communication means for communicating with a remote computer.

16. An apparatus for matching a fuel to a new engine design comprising:

a measurement means for measuring a value for at least one fuel property associated with the sample through a mid-infrared analysis;

a comparison means for comparing the value measured for the fuel property with a pre-estimated preferred value range for the fuel property for a new engine design;

a diagnosis means for diagnosing the fuel-related problem based upon a result of the comparison; and a display means for displaying a result of the diagnosis.

* * * * *